US005569285A

United States Patent [19]
Webb

[11] Patent Number: 5,569,285
[45] Date of Patent: Oct. 29, 1996

[54] SCALPEL WITH ROTARY DEPTH GUARD

[76] Inventor: Nicholas J. Webb, 5370 Basel Dr., Box 831, Wrightwood, Calif. 92397

[21] Appl. No.: 409,140

[22] Filed: Mar. 23, 1995

Related U.S. Application Data

[63] Continuation-in-part of Ser. No. 333,606, Nov. 2, 1994, abandoned.

[51] Int. Cl.$^6$ .......................... B26B 25/00; A61B 17/32
[52] U.S. Cl. ............................................. 606/180; 30/319
[58] Field of Search ...................... 606/180, 172, 606/167, 170, 179, 166; 30/292, 347, 319, 101–102, 128, 263, 298, 300, 306, 310, 422, 294; 111/82

[56] References Cited

U.S. PATENT DOCUMENTS

| | | | |
|---|---|---|---|
| 630,094 | 8/1899 | Noble | 30/319 |
| 756,213 | 4/1904 | Connell, Sr. | 30/319 |
| 1,080,038 | 12/1913 | Youngberg | 111/82 |
| 1,574,819 | 3/1926 | Jezler | 30/288 |
| 4,077,124 | 3/1978 | Christmann | 30/287 |
| 4,301,594 | 11/1981 | Okada | 30/292 X |
| 4,601,103 | 7/1986 | Sugiyama | 30/292 X |
| 4,791,928 | 12/1988 | Berke et al. | 30/319 |
| 4,887,598 | 12/1989 | Berke | 606/180 |
| 5,085,663 | 2/1992 | Tarr | 30/294 X |
| 5,101,564 | 4/1992 | Melter | 30/319 |
| 5,342,377 | 8/1994 | Lazerson | 606/166 |

OTHER PUBLICATIONS

Article on Rotatable Knife by Peter Michalos, MD, on p. 42 of Jun. 15, 1994 issue of Ocular Surgery News.

Primary Examiner—Michael Powell Buiz
Assistant Examiner—Nancy Mulcare
Attorney, Agent, or Firm—Jack Lo

[57] ABSTRACT

A scalpel includes a circular blade rotatably attached to one end of a handle. A circular depth guard having a diameter smaller than that of the blade is rigidly and coaxially connected thereto. The depth guard includes tractional knurls arranged around a rim thereof. Pressing the blade into a piece of tissue causes penetration thereinto until the depth guard engages the tissue. Pulling the scalpel along the tissue causes the depth guard to roll along thereon and rotate the blade, which makes a cut with a rolling motion that minimizes tissue adhesion and dragging for a smooth and even incision. The depth guard ensures that the blade cuts at a precisely known and perfectly even depth. The tractional knurls ensure reliable rotation of the depth guard and the blade even on wet and slippery tissue. In a second embodiment, a rotary depth guard is attached to a fixed blade. In both a third and a fourth embodiment, a circular rotary blade and a circular rotary depth guard are eccentrically mounted. When the depth guard is rolled along tissue, meshing gears rotate the blade at a high speed for a smooth incision.

7 Claims, 4 Drawing Sheets

SCALPEL WITH ROTARY DEPTH GUARD

This is a continuation-in-part of Ser. No. 08/333,606, filed Nov. 2, 1994, now abandoned.

BACKGROUND OF THE INVENTION

1. Field of the Invention

This invention relates generally to cutting implements, specifically to a scalpel with a rotary depth guard.

2. Prior Art

A typical surgical scalpel includes an extremely sharp, straight cutting blade, made of surgical-grade stainless steel, affixed to the end of a handle. The vast majority of scalpels are simple variations on the same basic shape. In use, the blade is pressed into the tissue to be cut, then pulled along the tissue to make an incision. As the blade slides pass tissue wet with body fluids, it tends to drag the tissue along because of surface adhesion. As a result, the tissue is distorted and cut slightly unevenly. The depth of the incision may also be uneven along its length, depending on the skill of the surgeon. Uneven incisions cause uneven pulling or bunching of the tissue during healing, so that excessive scaring may result. This is an acute problem for plastic and reconstructive surgeons, who are particularly concerned about minimizing scare tissue. Some surgical procedures, such as flap transfer, hair transplants, skin gratfs, and corneal incisions, require incisions at known and even depths—a precision that conventional scalpels cannot provide.

Surface adhesion or dragging can be minimized by using a rotary disc cutting blade that rolls along the tissue. Such rotary cutting implements have been extensively applied in a variety of uses, such as cutting cloth, paper, and food substances. A well known example is the rotary pizza knife that cuts through a pizza without dragging the cheese, similar to that shown in U.S. Pat. No. 630,094 to Noble (1899).

U.S. Pat. No. 1,574,819 to Jezler (1926) shows an animal skinning knife with a toothed-wheel that serves as a safety guard and guide for the cutting disc. The tips of the teeth extend beyond the perimeter of the cutting disc to allow a very shallow cutting depth. In use, the skinning knife is forced against the point of union between the hide and the flesh of a carcass to separate them. The bumpy rolling motion of the toothed-wheel causes the knife move up and down as it is pulled along, so that the cuts are uneven in depth.

Rotary cutting implements have also been specifically adapted for use in surgery. U.S. Pat. Nos. 756,213 to Connell (1904) and 4,791,928 to Berke et al. (1988) each shows a scalpel with a rotary disc blade. However, they include no provision for controlling the cutting depth, so that incisions of uneven depth can still be easily made. Furthermore, when the desired cutting depth is very shallow, and the surgical field is very wet and slippery, there is not enough friction between the blade and the tissue for properly rotating the blade. As a result, the rotary blade may be dragged along the tissue like a straight knife and produce an uneven incision.

Two rotatable blade scalpels are shown in U.S. Pat. No. 5,342,377 to Lazerson (1994) and the Jun. 15, 1994 issue of Ocular Surgery News. Each of these scalpels has a blade pivoted about an axis that lies on the plane thereof, so that the blades are rotatable for changing the direction of the cutting line with respect to the axis of the handle, i.e., these blades are primarily used for cutting circles. They do not rotate like wheels, so that they drag along the tissue in the same way as fixed blades. Furthermore, they have no provision for controlling penetration, so that they will produce incisions with uneven depths.

OBJECTS AND ADVANTAGES

Accordingly the primary objects and advantages of the present invention are to provide an improved surgical scalpel, a surgical scalpel which minimizes surface adhesion and dragging to provide smooth and even incisions that heal with minimal scarring, which provides a precisely known and perfectly even cutting depth along an entire incision, and which operates reliably at all cutting depths and in slippery surgical fields. Other objects and advantages will become apparent from a study of the following description of the invention.

SUMMARY OF THE INVENTION

In a first embodiment, the scalpel includes a circular blade rotatably held on the distal end of a handle. A circular depth guard, which is smaller in diameter than the blade, is coaxially attached to one side of the blade for limiting incisions to a known and even depth. The depth guard and the blade are rigidly connected for simultaneous rotation when they are pulled along tissue to be cut. The blade and the depth guard include traction knurls on one side and on the edge thereof, respectively, for ensuring reliable rotation of the blade on wet and slippery tissue. In a second embodiment, the scalpel includes a fixed blade with a rotary depth guard attached thereto. The depth guard rolls along a surgical field for eliminating friction therebetween, so that it does not contribute to tissue distortion. In both a third and a fourth embodiment, the scalpel includes a rotary depth guard eccentrically mounted adjacent a rotary blade. Meshing gears attached to the depth guard and the blade rotate the blade when the depth guard is dragged along tissue.

Drawing Reference Numerals

| | |
|---|---|
| 10. Circular Rotary Blade | 11. Depth Guard |
| 12. Axle | 13. Handle |
| 14. Knurls | 15. Incision |
| 16. Tissue | 17. Knurls |
| 18. Sleeve | 19. Flange |
| 20. Washer | 21. Washer |
| 30. Fixed Blade | 31. Handle |
| 32. Rotary Depth guard | 33. Axle |
| 34. Forward Cutting Edge | 35. Knurls |
| 36. Tissue | 37. Incision |
| 40. Handle | 41. Handle Side |
| 42. Handle Side | 43. Mounting Fork |
| 44. Pins | 45. Rotary Depth Guard |
| 46. Knurls | 47. Rim |
| 48. Axle | 49. Rotary Blade |
| 50. Washers | 51. Gear |
| 52. Axle | 53. Gear |
| 54. Rotary Depth Guard | 55. Knurls |
| 56. Rim | 57. Ring Gear |

DESCRIPTION—FIG. 1—FIRST EMBODIMENT

Figure 1:
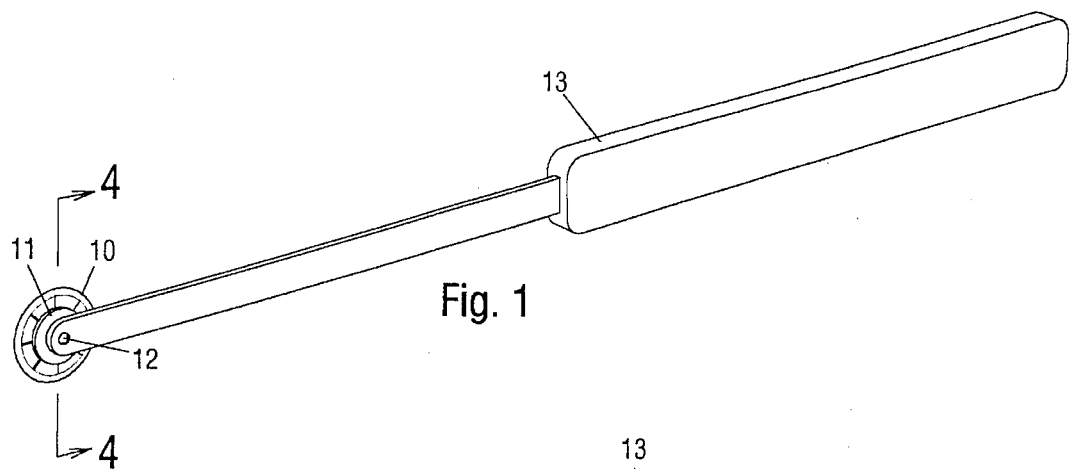
FIG. 1 is a side perspective view of a surgical scalpel with a rotary depth guard in accordance with a first embodiment of the invention.

In accordance with a first embodiment of the invention shown in the side isometric view in FIG. 1, a rotary scalpel includes a circular blade 10 and a circular depth guard 11 coaxially and rotatably held together by an axle 12 on the distal end of a handle 13. Blade 10 and depth guard 11 are rigidly attached to each other for simultaneous rotation.

DESCRIPTION—FIG. 2—FIRST EMBODIMENT

Figure 2:
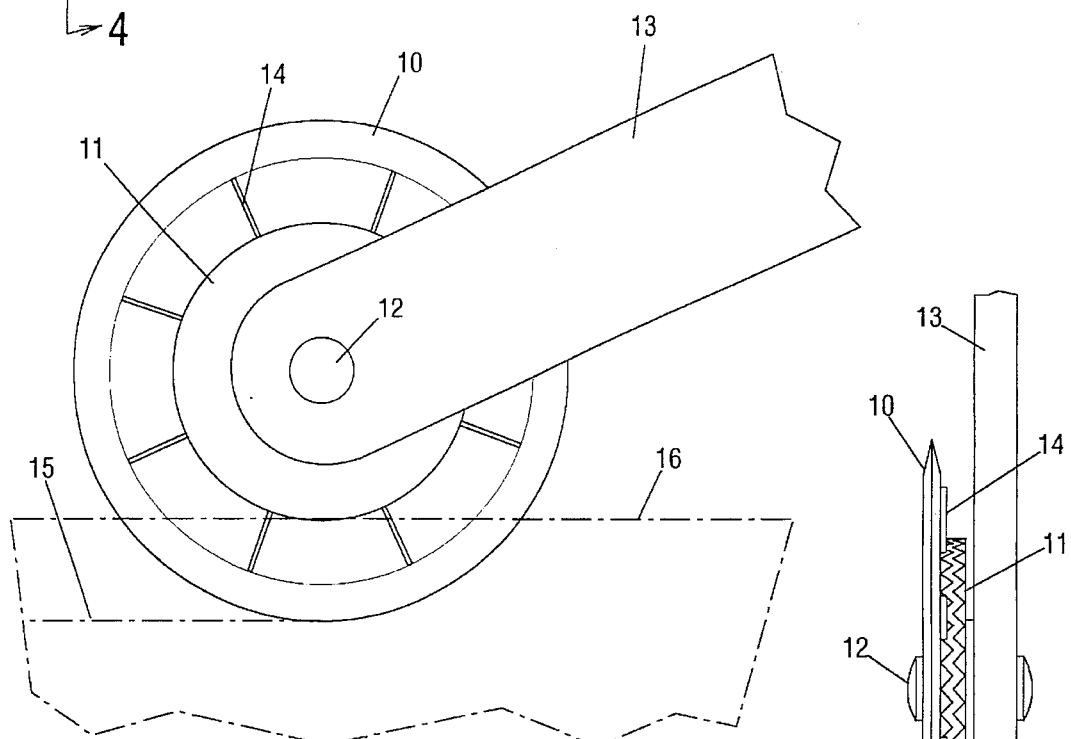
FIG. 2 is an enlarged side view of a circular blade of the scalpel.

As shown in the enlarged side view in FIG. 2, depth guard 11 limits penetration of blade 10 into a piece of tissue 16 up to the edge thereof. Pulling the scalpel along tissue 16 causes blade 10 to roll thereon and make an incision 15. This rotary cutting motion minimizes tissue adhesion and dragging for smooth and even incisions that heal with minimal scarring. Blade 10 includes raised ridges or knurls 14 arranged around one side thereof. Knurls 14 provide enough traction within incision 15 for reliable rotation of blade 10 when the scalpel is pulled along tissue 16.

DESCRIPTION—FIG. 3—FIRST EMBODIMENT

Figure 3:
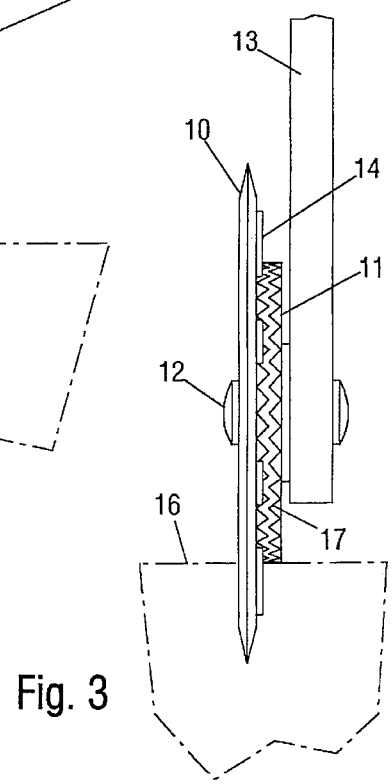
FIG. 3 is an enlarged front view of the circular blade of the scalpel.

As shown in the enlarged front view in FIG. 3, depth guard 11 includes knurls 17 arranged around its rim. Knurls 17 provide additional traction on tissue 16 for reliable rotation of depth guard 11 and blade 10 even if tissue 16 is very wet and slippery. Reliable rotation of blade 10 minimizes tissue adhesion and dragging for clean and smooth incisions that heal with minimal scarring.

Blade 10 and depth guard 11 can be made in different sizes for different types of surgery, and in different combinations of diameters for different cutting depths. For example, in one embodiment, blade 10 has a diameter of 8 mm, and depth guard 11 can be sized accordingly for providing a specific cutting depth that can range from 0.25 mm to 5 mm. Depth guard 11 ensures that each incision is made at a precisely known and perfectly even depth along its entire length, so that it will heal evenly, with minimal scarring.

DESCRIPTION—FIG. 4—FIRST EMBODIMENT

Figure 4:
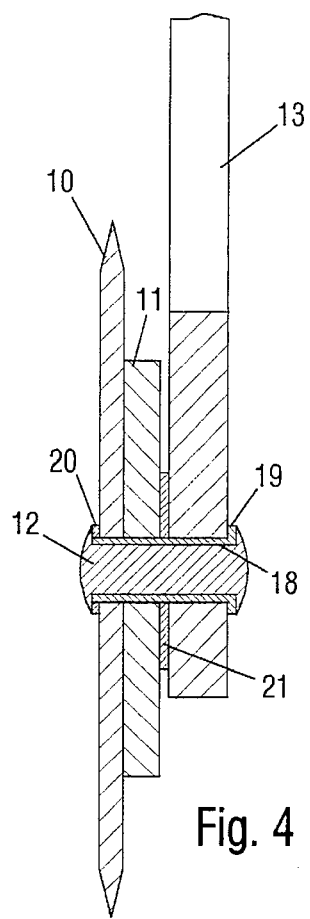
FIG. 4 is a front sectional view of the scalpel taken along line 4—4 in FIG. 1.

As shown in the from sectional view of the scalpel in FIG. 4, a sleeve 18 with a flange 19, and a washer 20 surround the shah of axle 12. A washer 21 is positioned between depth guard 11 and handle 13. Sleeve 18, washer 20, and washer 21 are made of a suitable low-friction material—such as those sold under the trademarks Nylon, Delrin, and Teflon—for ensuring easy and reliable rotation of blade 10 and depth guard 11.

DESCRIPTION—FIG. 5—SECOND EMBODIMENT

Figure 5:
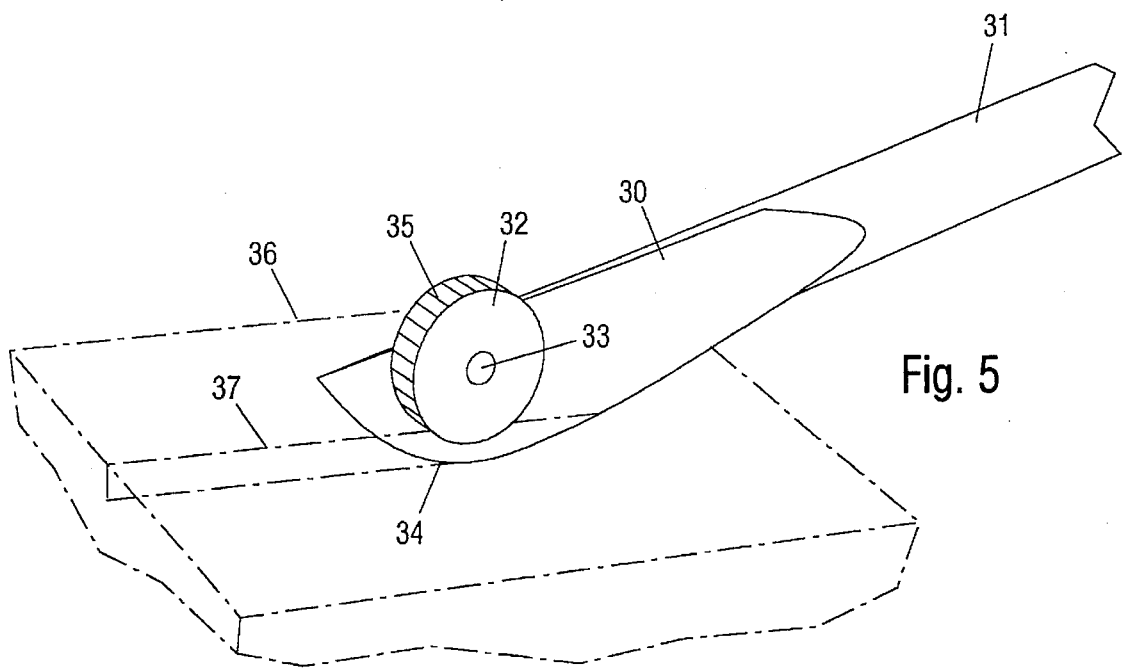
FIG. 5 is a side perspective view of a surgical scalpel with a rotary depth guard in accordance with a second embodiment of the invention.

In accordance with a second embodiment of the invention shown in FIG. 5, a scalpel includes a fixed blade 30 affixed to the distal end of a handle 31. A circular depth guard 32 is rotatably held on one side of blade 30 by an axle 33. The rim of depth guard 32 is spaced back from a forward cutting edge 34 of blade 30 by a predetermined distance for limiting the depth of incisions. Depth guard 32 includes knurls 35 arranged around its rim for traction on wet surgical fields. Depth guard 32 can be provided in different diameters for different cutting depths.

In use, pressing blade 30 into a piece of tissue 36 causes penetration until depth guard 32 engages the surface thereof. Pulling blade 30 along tissue 36 to make an incision 37 causes depth guard 32 to roll thereon. The rolling motion of depth guard 32 eliminates friction or dragging between itself and tissue 36, so that it will not contribute to tissue distortion and uneven incisions.

DESCRIPTION—FIG. 6—THIRD EMBODIMENT

Figure 6:
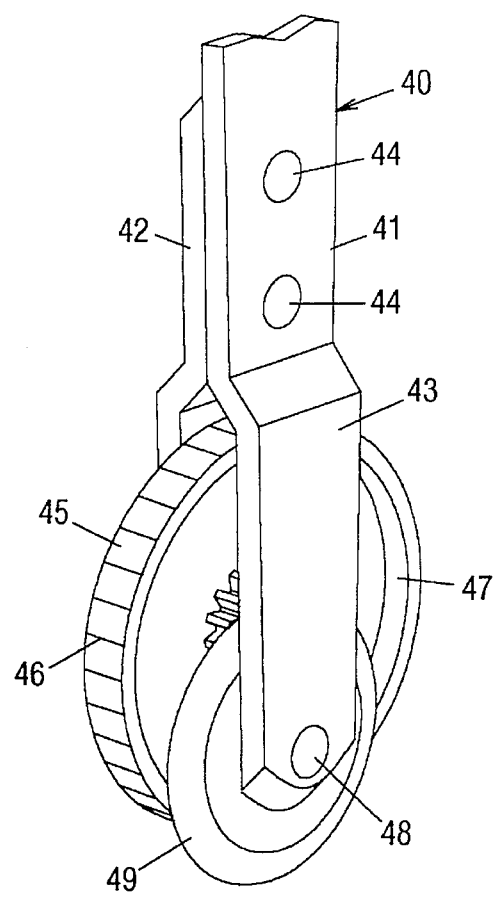
FIG. 6 is a side perspective view of a surgical scalpel with a rotary depth guard in accordance with a third embodiment of the invention.

In accordance with a third embodiment of the invention shown in FIG. 6, a scalpel includes a handle 40 (top end not shown) having two opposite sides 41 and 42 forming a mounting fork 43. Opposite sides 41 and 42 are attached together with a pair of pins 44. A circular rotary depth guard 45 having knurls 46 arranged around a rim 47 is rotatably mounted to handle side 42; the method of mounting will be explained in conjunction with FIG. 8. An axle 48 fixedly attached through the distal end of handle side 41 rotatably mounts a circular rotary blade 49 thereon.

DESCRIPTION—FIG. 7—THIRD EMBODIMENT

Figure 7:
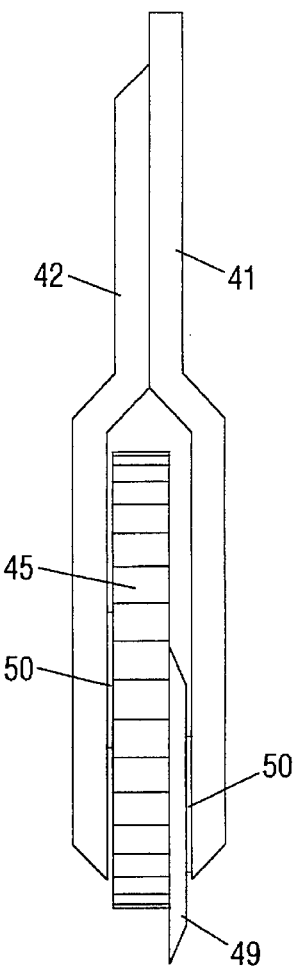
FIG. 7 is a from view of the third embodiment of the surgical scalpel.

As shown in the front view of the scalpel in FIG. 7, a pair of washers 50 are coaxially disposed between depth guard 45 and handle side 42, and between rotary blade 49 and handle side 41.

Figure 8:
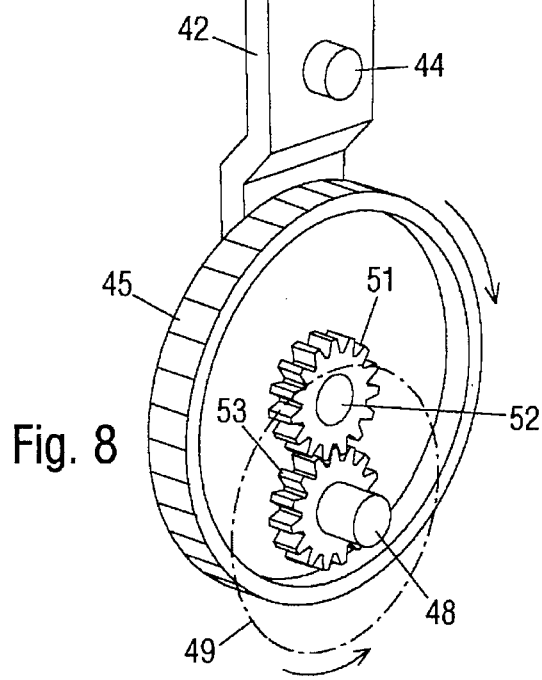
FIG. 8 is a partial cutaway side perspective view of the third embodiment of the surgical scalpel.

Description—FIG. 8—THIRD EMBODIMENT

To facilitate understanding, the scalpel is shown in FIG. 8 with rotary blade 49 in phantom line, and without handle side 41 (FIG. 6) and one of washers 50 (FIG. 7). An external gear 51 is fixedly and coaxially attached to the innerside of depth guard 45, which is rotatably mounted about an axle 52 extended therethrough and through gear 51. Axle 52 is fixedly attached to handle side 42. An external gear 53 is fixedly and coaxially attached to the innerside of rotary blade 49, which are both rotatably mounted on axle 48. Gear 53 is in meshing contact with gear 51.

In use, depth guard 45 precisely limits the cutting depth of rotary blade 49. Dragging the scalpel causes depth guard 45 to roll along the surgical tissue (not shown) and impart an opposite rotation to blade 49 through gears 51 and 53, as shown by the arrows. The ratio of rotation speeds between depth guard 45 and blade 49 is adjustable by varying the sizes of gears 51 and 53, e.g., blade 49 will rotate at a higher r.p.m. than depth guard 45 if gear 51 is larger in diameter than gear 53. Having blade 49 rotate faster than depth guard 45 simulates the effect of a motorized blade for very smooth incisions.

DESCRIPTION—FIG. 9—FOURTH EMBODIMENT

Figure 9:
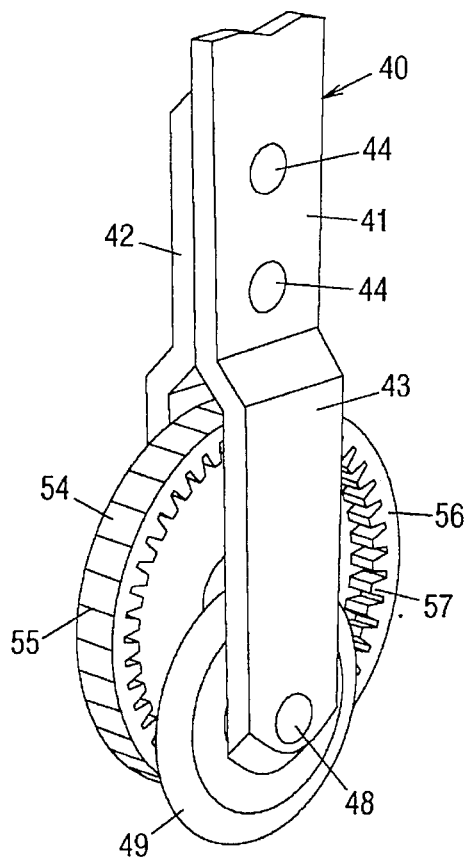
FIG. 9 is a side perspective view of a surgical scalpel with a rotary depth guard in accordance with a fourth embodiment of the invention.

In accordance with a fourth embodiment of the invention shown in FIG. 9, a scalpel includes a handle 40 (top end not shown) having two opposite sides 41 and 42 forming a mounting fork 43. Opposite sides 41 and 42 are attached together with a pair of pins 44. A circular rotary depth guard 54 having knurls 55 arranged around the outside of a rim 56 is rotatably mounted to handle side 42; the method of mounting will be explained in conjunction with FIG. 10. The inside of rim 56 forms an internal or ring gear 57. An axle 48 fixedly attached through the distal end of handle side 41 rotatably mounts a circular rotary blade 49 thereon.

DESCRIPTION—FIG. 10—FOURTH EMBODIMENT

Figure 10:
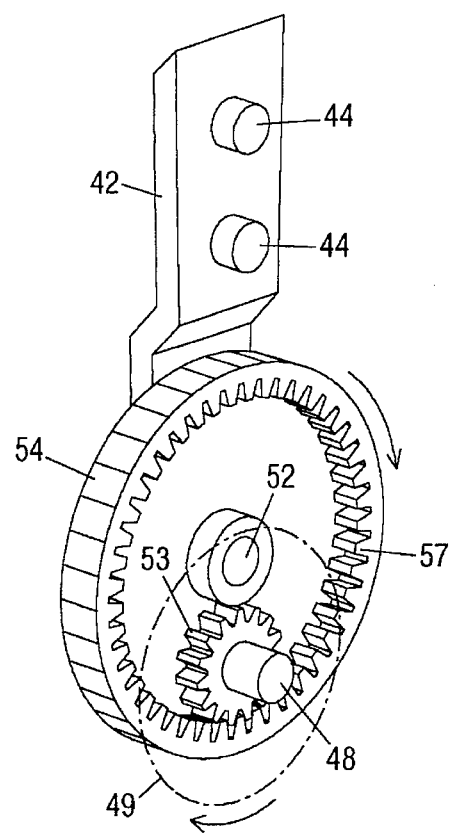
FIG. 10 is a partial cutaway side perspective view of the fourth embodiment of the surgical scalpel.

To facilitate understanding, the scalpel is shown in FIG. 10 with rotary blade 49 in phantom line, and without handle side 41 (FIG. 9). Depth guard 54 is rotatably mounted about an axle 52 extended therethrough and fixedly attached to handle side 42. An external gear 53 is fixedly and coaxially attached to the innerside of rotary blade 49, which are both rotatably mounted on axle 48. Gear 53 is in meshing contact with ring gear 57.

In use, depth guard 54 precisely limits the cutting depth of rotary blade 49. Dragging the scalpel causes depth guard 54 to roll along the surgical tissue (not shown), and impart a rotation to blade 49 through gears 53 and 57 in the same direction, as shown by the arrows. Because ring gear 57 has a much larger diameter than gear 53, blade 49 will rotate at a much higher r.p.m. than depth guard 54. This simulates the effect of a motorized blade for very smooth incisions.

Conclusion, Ramifications, And Scope

Accordingly the reader will see that I have provided an improved surgical scalpel. In the first embodiment, the rotary blade minimizes tissue adhesion and dragging for even and smooth incisions that heal with minimal scarring. It ensures that each incision is made at a precisely known and perfectly even depth along its entire length, and it will operate reliably even in wet and slippery surgical fields. In the second embodiment, the rotary depth guard eliminates friction or dragging between itself and the tissue, so that it does not contribute to tissue distortion and uneven incisions.

Although the above descriptions are specific, they should not be considered as limitations on the scope of the invention, but only as examples of the preferred embodiment. Many other ramifications and variations are possible within the teachings of the invention. For example, the handle can be angled or bow-shaped so that it will not block the surgeon's view of the cutting line. The blade can have either a bi-bevel or a single-bevel cutting edge. The permanent axle can be replaced with a removable fastener, such as a screw, so that the blade can be changed. The blade and the depth guard can be made in other sizes, and they can be separable and interchangeable, so that various combinations of different blades and depth guards can be provided. The knurls on the blade can be provided on both sides thereof, or they can be eliminated, so that the blade relies on the knurls on the depth guard for traction. Knurls of various shapes can be used on the blade and the depth guard. The rotary blade can be positioned between the depth guard and the handle. A pair of depth guards can be positioned on both sides of the blade. Different gearings can be provided for adjusting the rotation speed of the blade. In addition to surgery, the scalpel can be adapted for use in other applications. Therefore, the scope of the invention should not be determined by the examples given, but by the appended claims and their legal equivalents.

I claim:

1. A cutting implement, comprising:

a handle, a circular blade rotatably attached to said handle, a circular depth guard rotatably attached to said handle, a first gear fixedly attached to said circular blade, and a second gear fixedly attached to said circular depth guard and in engagement with said first gear, whereby rolling said circular depth guard along a member to be cut rotates said circular blade via said first and said second gears to make a smooth incision.

2. The cutting implement of claim 1 wherein said circular blade and said circular depth guard are eccentrically positioned.

3. The cutting implement of claim 1 wherein said first gear and said second gear are both external gears, so that said circular blade and said circular depth guard are arranged for opposite rotation.

4. The cutting implement of claim 1 wherein said first gear comprises an external gear and said second gear comprises a ring gear, so that said circular blade and said circular depth guard are arranged for rotation in the same direction.

5. The cutting implement of claim 1 wherein said handle includes a mounting fork at a distal end.

6. The cutting implement of claim 1 further including a plurality of knurls arranged around a rim of said circular depth guard for providing traction on said member to be cut.

7. A cutting implement, comprising:

an elongated handle, a circular blade rotatably attached to said handle, said circular blade having a predetermined diameter, and two sides a circular depth guard coaxially and fixedly connected to said circular blade for simultaneous rotation, said circular depth guard having a smaller diameter than said circular blade; and a plurality of knurls arranged on at least on side of the circular blade; and a plurality of knurls arranged around a rim of said circular depth guard;

whereby pressing said circular blade against a member to be cut causes penetration thereinto until said circular depth guard engages said member, and pulling said cutting implement along said member causes said circular depth guard to roll along thereon and rotate said circular blade to make an incision thereon with a rolling motion.

* * * * *